(12) United States Patent
Lloyd

(10) Patent No.: US 8,481,076 B2
(45) Date of Patent: Jul. 9, 2013

(54) BARIATRIC MAGNETIC APPARATUS AND METHOD OF MANUFACTURING THEREOF

(75) Inventor: Greg A. Lloyd, Spokane, WA (US)

(73) Assignee: Gorham Enterprises LLC, Westport, CT (US)

( * ) Notice: Subject to any disclaimer, the term of this patent is extended or adjusted under 35 U.S.C. 154(b) by 594 days.

(21) Appl. No.: 12/127,109

(22) Filed: May 27, 2008

(65) Prior Publication Data

US 2008/0292691 A1  Nov. 27, 2008

Related U.S. Application Data

(60) Provisional application No. 60/931,791, filed on May 25, 2007.

(51) Int. Cl.
*A61K 9/48* (2006.01)
*A61K 38/16* (2006.01)
*A61P 3/04* (2006.01)

(52) U.S. Cl.
USPC .......................................... 424/451; 514/1.1

(58) Field of Classification Search
None
See application file for complete search history.

(56) References Cited

U.S. PATENT DOCUMENTS

| 5,017,381 A | 5/1991 | Maruyama et al. |
| 5,417,976 A | 5/1995 | Peery et al. |
| 5,563,511 A | 10/1996 | Van Fleet, III |
| 6,627,206 B2 * | 9/2003 | Lloyd ............................ 424/400 |
| 6,656,194 B1 | 12/2003 | Gannoe et al. |
| 7,497,822 B1 | 3/2009 | Kugler et al. |
| 2002/0183768 A1 | 12/2002 | Deem et al. |
| 2003/0021822 A1 | 1/2003 | Lloyd |
| 2006/0134978 A1 | 6/2006 | Rosen et al. |
| 2006/0266370 A1 | 11/2006 | Tan |
| 2007/0010164 A1 | 1/2007 | Kowalski |
| 2009/0036351 A1 * | 2/2009 | Boots ................................ 514/2 |

FOREIGN PATENT DOCUMENTS

GB  547668  9/1942

OTHER PUBLICATIONS

John Hopkins University News Release, Tiny Self-Assembling Cubes Could Carry Medicine, Cell Therapy, Dec. 13, 2005, retrieved Jul. 15, 2008, from http://www.jhu.edu/news/home05/dec05/cubes.html, 5 pages.
John Hopkins University (Dec. 13, 2005), Tiny Self-assembling Cubes Could Carry Medicine, Cell Therapy, Scient Daily, Retrieved Jul. 15, 2008, from http://www.sciencedaily.com/releases/2005/12/051213073243.htm, 3 pages.
International Search Report and Written Opinion for PCT/US2008/064849 dated Aug. 27, 2008, 11 pages.
EP Application No. EP08756289, Supplementary European Search Report dated Oct. 30, 2012, 4 pages.

* cited by examiner

*Primary Examiner* — Suzanne Ziska
(74) *Attorney, Agent, or Firm* — Cantor Colburn LLP

(57) ABSTRACT

A bariatric procedure or delivery apparatus is configured in such a way to deter premature passing of magnetic members through the pylorus. In other exemplary embodiments, the magnetic apparatus includes a plurality of magnetic members, having one of a variety of configurations, wherein plural magnetic poles are disposed on a surface of the apparatus.

25 Claims, 11 Drawing Sheets

BARIATRIC MAGNETIC APPARATUS AND METHOD OF MANUFACTURING THEREOF

CROSS REFERENCE TO RELATED APPLICATIONS

The present application claims priority to U.S. Provisional Application Ser. No. 60/931,791 filed May 25, 2007, the entire contents of which are specifically incorporated herein by reference.

TECHNICAL FIELD

This disclosure relates to a therapeutic apparatus, and more particularly to an apparatus pertaining to the promotion of weight loss.

BACKGROUND

Year after year, the amount of cases of obesity among both adults and children has been drastically on the rise in epidemic proportions. Obesity is both an individual clinical condition and is increasingly viewed as a serious public health problem. The adverse health consequences of obesity are well known and established. In particular, obesity has been linked to a predisposition to various health conditions and diseases including cardiovascular disease, diabetes, dyslipidemia, gallbladder disease, and even some types of cancers. Even though the health consequences of being obese are serious, many are unable or unwilling to lose weight on their own volition.

Over the past several years, various weight loss programs, exercise equipments, diets and bariatric treatments have been developed in order to combat the obesity epidemic. These solutions are often ineffective for long-term weight loss or may even include serious health risks. Unfortunately for many, the bariatric treatments require extremely risky and costly invasive surgical procedures.

A method of weight loss for morbidly obese patients as described by commonly owned U.S. Pat. No. 6,627,206, the entire contents of which are specifically incorporated herein by reference, involves the ingestion of magnetically self-tessellating, space-filling polyhedrons (hereinafter referred to as "magnetic cubes," or "cubes"). In exemplary embodiments therein, approximately 80% of the patient's gastric lumen is displaced by the non-digestible cubes that semi-permanently reside within the stomach. The therapeutic effect is similar to stomach stapling, gastroplasty, and similar restrictive surgeries but requires no surgery and is reversible via an endoscopic procedure under conscious sedation.

The tessellated aggregate can also be gradually produced over time by the patient at home. For instance, in one embodiment of the above described procedure, the patient would be prescribed a quantity of capsules, each containing two magnetic cubes measuring 8.4 mm across their flats. The patient would swallow eight capsules with each meal (four times a day) for one month. After 30 days, the patient's gastric lumen would have 80% of its volume—roughly 1.2 liters—occupied by the cubes.

The above-described procedure does have drawbacks, however, as any near-round object that can make its way down the esophagus can also pass through the pylorus and exit the gastric lumen (stomach). What is needed is an improved procedure that retains the benefits described above, but that also remedies problems associated with the cubes prematurely passing through the pylorus. Additionally, there is room for improvement on the design of the cubes and delivery mechanism used for the bariatric treatment.

SUMMARY

The above discussed and other disadvantages of the art are overcome and alleviated by the present bariatric procedure and delivery apparatus. In exemplary embodiments, the bariatric procedure or delivery apparatus is configured in such a way to deter premature passing of magnetic members through the pylorus. In other exemplary embodiments, the magnetic apparatus includes a plurality of magnetic members, having one of a variety of configurations, wherein plural magnetic poles are disposed on a surface of the apparatus.

In one exemplary embodiment, to ensure that the initial (first day) tessellated structure is too large to pass through the pylorus and to prevent bowel obstructions, the administering physician requires that the patient swallow a certain, minimum number of capsules along with a slow-digesting liquid meal (such as a high-protein drink) at the physician's office before allowing the patient to leave. Thereafter, the capsules may be self-administered on an outpatient basis. For example, for cubes measuring 8.4 mm across their faces, swallowing 48 twin-cube capsules in the physician's office would produce an initial seed aggregate measuring roughly 4.8 cm across; too large to transit the pylorus.

The use of a high-protein food (chewable or liquid) at the physician's office increases residency time within the stomach to help ensure that the cubes find a stable, good site on the main aggregate onto which to tessellate before the pylorus opens again. This technique exploits the prime role of the stomach: it is the first stage in the digestion of proteins. The hydrochloric acid in the stomach denatures proteins (uncoils them) and the stomach enzyme pepsin cleaves them at various locations into polypeptides. After the stomach has done its job on proteins, the stomach's contents (chyme) are then passed onto the small intestines where the polypeptides are fully cleaved into amino acids by a host of other peptidases.

After the first day's initial aggregate is formed in the physician's office under supervision, the patients may be instructed to swallow, for example, eight caplets (16 cubes) immediately after each meal until they are all consumed (a month-long process). The patient may further be instructed that their meals must contain protein and that caplets should not be swallowed on an empty stomach or after any meal or snack containing no protein. For instance, a confection such as a sugar-free Popsicle (mostly water, 6% carbohydrates, and zero protein) would pass through the stomach very quickly. Failure to observe these instructions could, at best, lead to wasted cubes that are excreted in the stools. At worst, a bowel obstruction might result.

The present invention also recognizes that patient adherence to dietary instruction is often poor. With that in mind, a significant percentage of patients being treated with the magnetic cubes can be expected to ingest their caplets with inappropriately low protein in their stomachs. This would create a risk for associated complications as described above. To meet this challenge, another exemplary embodiment of the invention described herein entails delivering a peptide-bearing substance, such as protein, along with the magnetic cubes.

This can be accomplished for example, by imbedding the cubes within a dry-compressed, protein-bearing tableting formulation or by placing both protein powder and the cubes inside a gelatin capsule, among other configurations. Accordingly, a bariatric delivery apparatus may be formed. The methods described herein might, for example, provide about two to three grams of protein with each post-meal dose.

Considering that a typical diet for a normal-weight person requires 15 grams per meal (60 g/day), two to three grams is enough protein for the stomach to sense and cause the appropriate closure of the pyloric sphincter.

BRIEF DESCRIPTION OF THE DRAWINGS

The above and other aspects, features and advantages of the present invention will become more apparent by describing in detail exemplary embodiments thereof with reference to the attached drawings, in which.

DESCRIPTION OF EXEMPLARY EMBODIMENTS

Figure 1:
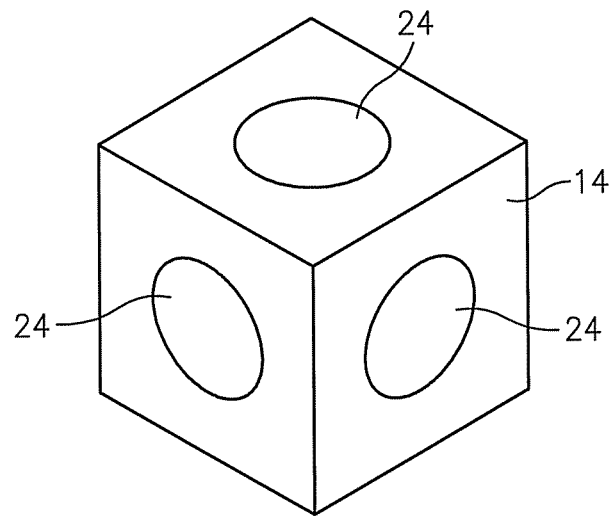
FIG. 1 is a front perspective view illustrating a magnetic apparatus according to an exemplary embodiment of the present invention.
Figure 2:
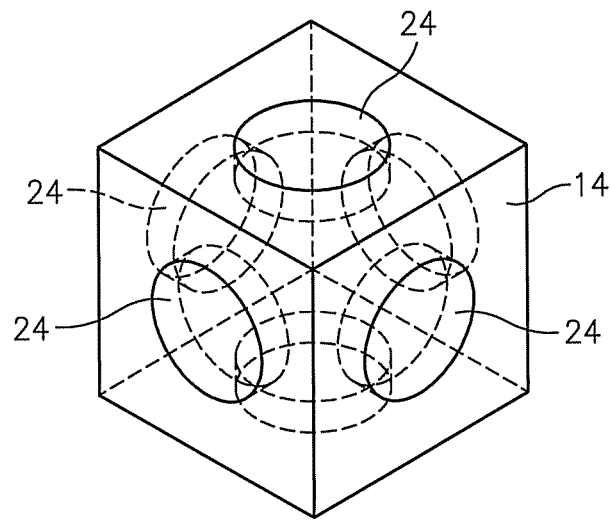
FIG. 2 is a front perspective view illustrating a plurality of cavities within a magnetic apparatus according to an exemplary embodiment of the present invention.
Figure 3:
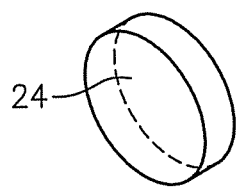
FIG. 3 is a front perspective view illustrating a magnetic member according to an exemplary embodiment of the present invention.
Figure 4:
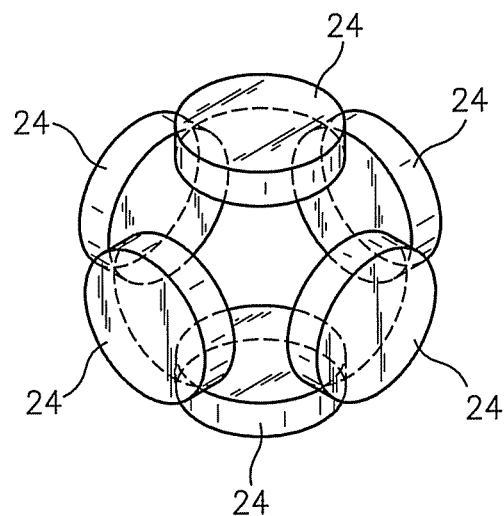
FIG. 4 is a front perspective view illustrating a configuration of magnetic members according to an exemplary embodiment of the present invention.

As is noted above, the present bariatric procedure and delivery apparatus is configured in such a way to deter premature passing of magnetic members through the pylorus. This may comprise a procedure requiring a predetermined amount of protein or the like so as to cause closure of the pyloric sphincter, or it may comprise a bariatric delivery apparatus that integrates a magnetic member with a predetermined amount of protein or the like. As will be discussed immediately below, the bariatric delivery apparatus may comprise any of a number of ingestible shapes.

In an exemplary embodiment, the bariatric delivery apparatus is sphere shaped. In another exemplary embodiment, the multiple-poled magnet of the bariatric delivery apparatus consists of four-poles. In another exemplary embodiment, the multiple-poled magnet of the bariatric delivery apparatus consists of six-poles. In another exemplary embodiment, the multiple-poled magnet of the bariatric delivery apparatus consists of eight-poles. In another exemplary embodiment, the retaining structure of the bariatric delivery apparatus is cube shaped. In another exemplary embodiment, the retaining structure of the bariatric delivery apparatus is sphere shaped.

In another exemplary embodiment, the retaining structure of the bariatric delivery apparatus is pill shaped which encapsulates a cubic shaped retaining structure enclosing a six-poled magnet.

Different delivery mechanisms are also contemplated, For example, in another exemplary embodiment, the bariatric delivery apparatus is administered to a patient via an endoscopic scope. In another exemplary embodiment, the bariatric delivery apparatus is retrieved from a patient via an endoscopic scope.

Also, the bariatric delivery apparatus may comprise any number of materials. For example, in another exemplary embodiment, a portion of the bariatric delivery apparatus comprises a foamed polymer material. In another exemplary embodiment, the bariatric delivery apparatus is a foamed polyolefin material. In another exemplary embodiment, the bariatric delivery apparatus is a foamed polyproyburine material.

In another exemplary embodiment, the bariatric delivery apparatus has a combined density of less than 1.0. In another exemplary embodiment, the bariatric delivery apparatus has a combined specific gravity of greater than 1.0.

In another exemplary embodiment, the bariatric delivery apparatus is covered with a protective material. For example, in an exemplary embodiment, the bariatric delivery apparatus is covered with a protein/peptide shell to protect the bariatric delivery apparatus from bodily fluids and to promote closure of the pyloric sphincter.

Pepsin is most efficient at cleaving protein bonds at the carboxy side of the aromatic amino acids such as phenylalanine and tyrosine. Pepsin is most active at cleaving the following amino acid bonds: Phe1–/–Val, Gln4–/–His, Glu13–/–Ala, Ala14–/Leu, Leu15–/–Tyr, Tyr16–/–Leu, Gly23–/–Phe, Phe24–/–Phe. However, many peptides or polypeptides could theoretically be substituted for a protein. Accordingly, the term "protein/peptide" herein refers to protein or any suitable peptide or polypeptide that can be acted upon by pepsin, or any combination of the three.

There are 21 "standard" amino acids (those with the L-configuration) that are encoded by DNA, but there are more than 500 naturally occurring amino acids. The $21^{st}$ amino acid was only recently discovered so many sources still show that there are only twenty. Peptides consist of two or more amino acids chained to each other via peptide linkages. Polypeptides consist of ten to fifty amino acids. Proteins contain more than fifty amino acids. The demarcation between polypeptides and proteins is rather arbitrary, and the scope of the invention described herein is not meant to be limited by either.

Also, the term "solid oral dosage unit" refers broadly to the entire class of solid, pill-like compositions in the various forms suitable for oral administration, including tablets, but the term as used here refers particularly to capsules and caplets. A capsule may a torpedo-shaped gelatin carrier containing a formulation. Caplets may be solid tablets comprising a formulation (with or without a coating) compressed into the shape of a capsule.

There are several techniques whereby protein/peptide can accompany cubes (again, the term "cubes" as used herein refer to the magnetic element and carrier, but in no cases restrict the shape of the carrier (i.e., the "cube" may be cubic, spheric, etc.) while being ingested: 1) wherein each solid oral dosage unit containing one or more cubes also incorporates a protein/peptide formulation (hereinafter referred to as "auto-accompanying protein/peptide"), 2) where solid oral dosage units containing cubes are distinct and separate from those that incorporate the protein/peptide formulation (hereinafter referred to as "dedicated protein/peptide"), and 3) a combination of these two techniques.

Auto-Accompanying Protein/Peptide

One way to ensure that a protein/peptide dose is administered whenever cubes are ingested is to incorporate a protein/peptide formulation in each solid oral dosage unit containing one or more cubes. With gelatin capsules, such a scheme doesn't require any special mechanical properties for the protein/peptide formulation. For instance, a pure, compacted powder such as micellar casein (a milk protein produced via a special process that doesn't denature the protein) can simply occupy the free volume within the capsule.

Figure 9:
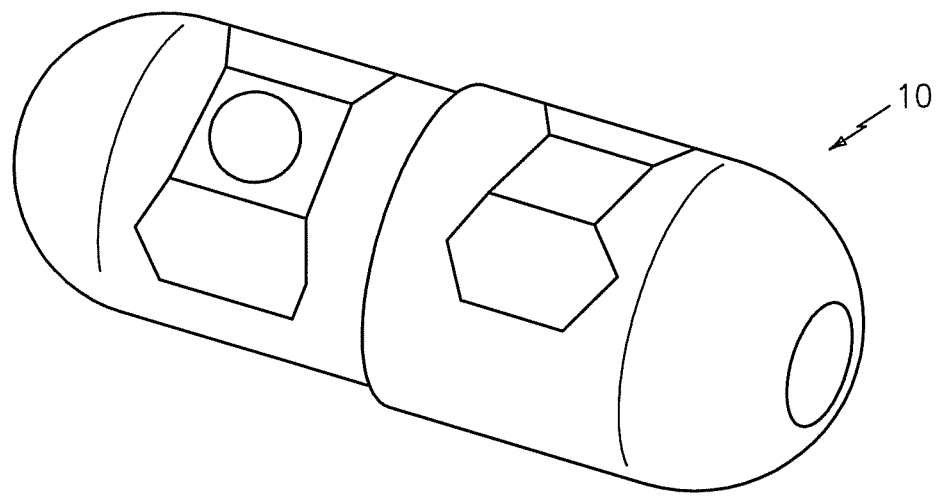
FIG. 9 is a perspective view of an exemplary caplet bariatric delivery apparatus.
Figure 10:
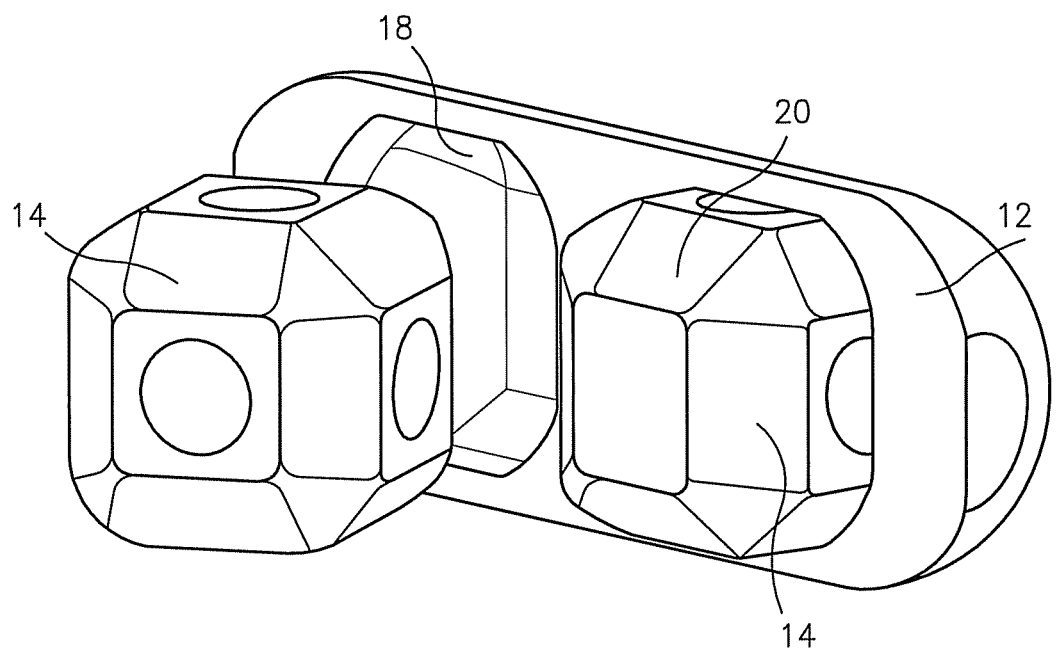
FIG. 10 is a cut-away cross view of an exemplary caplet bariatric delivery apparatus showing two exemplary magnetic cubes housed therein.

Reference is made to FIG. 9 and FIG. 10, which depict the auto-accompanying technique as implemented with both capsules and caplets. In the illustrated exemplary embodiment of FIG. 9, A single, size-000 capsule (gelatin capsule), which is shown generally at 10, containing two cubes can also contain 250 mg of a protein powder such as micellar casein. Eight of these swallowed with a meal would deliver 2 g of protein.

In the illustrated exemplary embodiment of FIG. 10, a cutaway is illustrated showing a cube-bearing caplet 12. The high compaction densities that can be achieved via the tableting process, combined with the full utilization of all available volume, permits as much as 375 mg of protein, such as micellar casein, per caplet. Eight of these—along with their sixteen cubes 14—would deliver 3 g of protein.

As can readily be seen in FIGS. 9 and 10, adding protein/peptide within each solid oral dosage unit automatically ensures that protein will also be simultaneously introduced into the stomach as the cubes 14 are delivered. No extra diligence on the patient's part is required. Eight caplets 12 of the type shown in FIG. 10 would deliver up to 3 g of protein/peptide after a meal.

The following describes an exemplary process for filling a gelatin capsule. Gelatin capsules are two-part assemblies comprising a body and cap. Alternating layers of cubes and protein/peptide may be dispensed into the capsule body and then the cap may be slipped over it. Alternatively, tableted preforms can be interleaved with cubes within the capsule body in place of a free-flowing powdered or granulated product.

Tableting entails the compression of ingredients to create a solid tablet or caplet. Tableting is accomplished via processes such as wet granulation, dry granulation, and direct compression. The active pharmaceutical ingredient (API) by itself rarely, if ever, has all the desired physical properties necessary for handling and compaction into a tablet. This is why excipients are added to tableting formulations. Excipients are substances, other than the API, that are included in a formulation to aid in the manufacturing process; or to add bulk, protect, support, enhance stability, bio-availability or patient acceptability, assist in product identification, or enhance any other attributes of the overall safety and effectiveness of the drug delivery system during storage or use. Excipients necessarily dilute the API. However, for many medicaments, dosages of the API are measured in micrograms so dilution is actually desirable because it increases the bulk of the tablet to practical proportions. In certain embodiments of the present invention however, the maximum concentration of protein/peptide is desired. Accordingly, the proportion of excipients in an auto-accompanying caplet may be kept to a minimum. Even though the protein/peptide is necessarily diluted by excipients, the high density achieved due to compaction during the tableting process partially offsets this dilution effect, producing relatively high volumetric yields of protein/peptide.

Dedicated Protein/Peptide

Another way to ensure that protein/peptide is present in the stomach whenever cubes are ingested is to provide special, dedicated solid oral dosage units containing, or entirely comprising, a protein/peptide formulation. These would be distinct and separate from those containing the cubes. The two different types of solid oral dosage units would be swallowed at one sitting after a meal.

Figure 11:
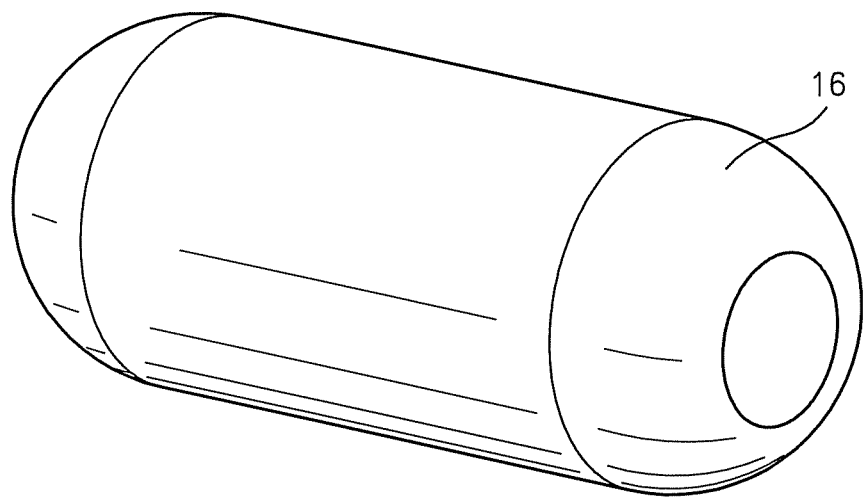
FIG. 11 is a perspective view of an exemplary caplet bariatric delivery apparatus.

Given the reality of low adherence to dietary instruction by many patients, this technique will work most effectively when both types of solid oral dosage units are grouped together in special packaging, such as foil blister packs. Such packaging provides convenient, pre-determined, per-meal dosages and ensures that both types of solid oral dosage units are simultaneously delivered in the proper proportions. For instance, one blister pack of twelve solid oral dosage units could comprise eight gelatin capsules containing only cubes (not pictured) plus four caplets comprised of a protein/peptide-based formulation (See FIG. 11, which shows a single, dedicated caplet 16 comprised entirely of a casein/excipients formulation can deliver 750 mg of micellar casein. Four of these caplets 16 would provide 3 g of protein. Cube-bearing caplets made via the tableting process as shown in FIG. 10—but not cut away—might also appear identical to this illustration). In this example, each blister pack could deliver, e.g., sixteen cubes and up to about three grams of protein/peptide. All the patient has to remember is to consume one entire blister pack of twelve solid oral dosage units after a meal.

Alternatively, a combination of the dedicated and auto-accompanying protein/peptide techniques could be employed. For instance, a ten-piece blister pack could consist of eight, auto-accompanying, cube-bearing capsules 10 or caplets 12 (FIG. 9, or FIG. 10 and FIG. 11) each containing 250 to 375 mg of protein/peptide, as well as two dedicated protein/peptide caplets 16 (FIG. 11) each containing 750 mg of protein/peptide. The total protein/peptide delivered would as great as 4.5 g per ten-piece package.

Formulation

Any number of protein/peptide sources may be used in tableting and capsule formulations. Micellar casein and soy protein isolate are good examples. Neither is denatured so the pepsin in the stomach must spend the maximum amount of time breaking down these proteins. Casein has the advantage that its aqueous solutions can serve as glues to bond together multipart capsule assemblies without exposing the magnetic cubes to the high compaction pressures. Casein's disadvantage is that it is contraindicated for those with milk allergies.

One exemplary embodiment for a protein/peptide tableting formulation suitable for direct compression is as follows:

TABLE 1

| Ingredient | Function | Proportion by weight |
|---|---|---|
| Microcrystalline cellulose | Tablet binder | 49% |
| Micellar casein | Protein | 42% |
| Sodium bicarbonate | Binary disintegrant/binary adjuvant | 4.011% |
| Citric acid | Binary disintegrant/binary adjuvant | 1.529% |
| Croscarmellose sodium | Disintegrant | 2% |
| Colloidal silicon dioxide | Flow agent | 1.21% |
| Sodium stearyl fumarate NF | Lubricant | 0.25% |

At a tableting pressure of only 25 N/c-mm (newtons per circular millimeter, equivalent to 32 MPa and 4600 psi), the above direct-compression tableting formulation possesses good strength and disintegrates very quickly in the stomach.

As regards bonding together multipart caplet assemblies using a casein-based glue, the tableting pressure of 32 MPa exceeds an exemplary 10 MPa crush strength of the magnetic cubes. A "circular millimeter" is simply a diameter, in millimeters, squared. Circular millimeters are just a convenient measure of area, as it avoids the complexity of calculating true area (one-half diameter, squared, times pi). For any true area in $mm^2$, the value in c-mm is always 27.324% greater. Any pressure expressed in N/c-mm can be converted to megapascals (MPa) by multiplying the c-mm value by 1.27324.

As shown in the above table, citric acid ($C_6H_8O_7$) and sodium bicarbonate ($NaHCO_3$) serve as a binary disintegrant. A single mole of citric acid plus three moles of sodium bicarbonate combine to form one mole of sodium citrate ($Na_3C_6H_5O_7$), three moles water ($H_2O$), and three moles of carbon dioxide ($CO_2$). This stoichiometric, 3:1 molar ratio of sodium bicarbonate:citric acid equates to a 1.312:1 ratio by mass. The sodium bicarbonate:citric acid mass ratio in the example of TABLE 1 is a 2.62:1. It is doubly rich in sodium bicarbonate. This ratio, in combination with crosscarmellose sodium, exhibits excellent disintegration performance in simulated gastric juice after a light meal (pH 3.0 HCl at 37° C.). The present disclosure believes that that the extra sodium bicarbonate reacts with hydrochloric acid in the stomach and helps to ensure that sufficient sodium bicarbonate is available to react with the citric acid.

The sodium bicarbonate/citric acid binary disintegrant has a dual function as shown in the above table: it is also a binary adjuvant. In this case, it is the sodium citrate byproduct that is the actual adjuvant. Sodium citrate may be used for relief of upset stomach due to overeating. Sodium citrate is also a buffering agent (antacid). The ability to settle an upset stomach is advantageous for certain embodiments of the present invention. In exemplary embodiments, an after-meal dosage of eight caplets 12 of the type shown in FIG. 10 (Ø 10.0 mm×26.6 mm), and formulated per TABLE 1 as shown above, would provide up to 150 mg of sodium citrate. The maximum conceivable after-meal dosage of 24 of these caplets would provide up to 450 mg of sodium citrate. Thus, the amount of sodium citrate delivered by this invention could provide mild to moderate relief of upset stomach due to overeating.

An adjuvant is an ingredient that facilitates or modifies the action of the API. As can be seen above, there are two exemplary ways to introduce sodium citrate into the stomach: it can be created within the stomach, or it can be directly delivered to the stomach.

Another preferred embodiment for cube-bearing gelatin capsules is to fill the available free space with pure granular or powdered protein such as micellar casein or soy protein isolate. Caplets could also be coated with a coating, such as one of BASF's Kolicoat products, to facilitate swallowing and prevent the caplet from disintegrating in the esophagus.

Exemplary Bariatric Caplet Magnet Constructions

There are a number of alternative configurations that may be made to effect embodiments of the present invention utilizing bariatric caplets. The following should be construed as being merely exemplary, and not limiting in any way.

There are ten interrelating factors which influence the design of the magnets inside of the bariatric cubes: weight, magnetic strength, corrosion resistance, toxicity, cost, ease of fabrication, ease of magnetization, ease of being handled while being overmolded, ability to withstand overmolding temperatures, and the ability to be degaussed (demagnetized) externally to the patient.

Material: Alnico and Ease of Demagnetization

Referring now to TABLE 2 below, the first material, cast alnico 5, has good magnetic strength (column A) of the alnico series that could still be readily demagnetized; that is, it has low resistance to being degaussed (column G).

TABLE 2

| | COMPARISON OF MATERIALS | | | | | | |
|---|---|---|---|---|---|---|---|
| | A | B | C | D | E | F | G |
| Property | Magnetic Strength | Max. Molding Temp. | Gastric Corrosion Resistance | Cytotoxic Potential | Limiting Element (amount) | Rel. Cost | Degaussing Resistance[1] |
| Technical name | Max Energy Product | Max. Operating Temp | Maximum Exposed Magnet Area | Max. Allowable Leach Rate | | | Minimum Intrinsic Coercivity |
| Variable's Symbol | $BH_{max}$ | $T_{mo}$ | | | | | $H_{ci}$ |
| Unit | MGOe | °C. | $mm^2$ | mg/day | Symb. (mg/day) | | kOe |
| Cast Alnico 5 | 5.5 | 550 | 4,500[B] | 8.2 | Co (2) | 0.6 | 0.64 |

TABLE 2-continued

COMPARISON OF MATERIALS

|  | A | B | C | D | E | F | G |
|---|---|---|---|---|---|---|---|
| S2612 | 26 | 300 | (Good) | 7.7 | Co (2) | 2.5 | 12[C] |
| N4220-SH | 42 | 150 | (Poor[2]) | 16.7 | Fe (10) | 1.15 | 20[C] |
| N4514-M | 45 | 80 | (Poor[2]) | 16.7 | Fe (10) | 1 | 14[C] |

The magnet materials listed above have the following conversational names: S2612 is called "samarium-cobalt"; N4220-SH and N4514-M are both called "neodymium."
[1]A demagnetizing force 50% greater than the material's $H_{ci}$ is required to sufficiently permanently demagnetize magnets.
[2]Backup coating of Parylene required
[B]At a pH of 2.5
[C]This value is well beyond the ability of any feasible degaussing machine capable of projecting the field 38 cm from the coil.

Note the circled values in TABLE 3 below. The magnetic strength of cast alnico 5 is 5.5 MGOe (pronounced "megagauss oersteds") and has a resistance to being demagnetized of only 640 Oe (0.64 kOe). This is not much more than cast alnico 1, 2, and 3. However, the resistance to being demagnetized rapidly strengthens for grades better than alnico 5. The alnico 5DG and 5-7 are proprietary grades from a particular manufacturer. So the next step up in a commodity grade is alnico 6, which has significantly greater intrinsic coercivity.

Materials with low resistance to being demagnetized may be desired because if a patient developed complications and was still ambulatory, he or she could simply go to a facility equipped with a custom, very powerful degaussing (demagnetizing) machine. There, the patient could stand up against a 15-inch-diameter electric coil for demagnetization. Literally, they would feel a half-second-duration vibration inside their stomach and that's all there would be to it. The doctor would tell them "Go home and sit on the toilet whenever you feel the urge."

The challenge with degaussing cubes that are inside a patient is in projecting a sufficiently strong degaussing field across the long distance necessary with extremely obese individuals. Besides being large, a morbidly obese individual can have a unique habitus (overall shape and arrangement of their internal organs). Their gastric organ (the true "stomach" organ) can be located near the front left of the abdomen like most people. Alternatively, it can be distended and large portions may be located towards their spine. Accordingly, a field strength of 1000 Oe in a "ringing," (rapidly decaying, sinusoidal) waveform may be used to project 38 cm from the coil in order to reach through the patient and demagnetize the cubes wherever they might be.

Alternate embodiments contemplate an endoscopic procedure under conscious sedation to remove cubes if complications develop.

Split Open Caplet and Magnet's Mass Limit: Volume

FIG. 10 shows the fundamental physical limitation that constrains the magnet's volume and mass: the maximum diameter of a caplet that can be readily swallowed. Capsules and caplets commonly on the market do not exceed a diameter

TABLE 3

ALNICO GRADES

| Material Grade | Composition | | | | | | Magnetic Properties | | | | | | | |
|---|---|---|---|---|---|---|---|---|---|---|---|---|---|---|
| | | | | | | | Max Energy Product $BH_{max}$ | | Residual Induction $B_r$ | | Coercivity $H_c$ | | Intrinsic Coercivity $H_{ci}$ | |
| | Fe | Al | Ni | Co | Cu | Ti | (MGOe) | (kJ/m³) | (kG) | (mT) | (Oe) | (kA/m) | (Oe) | (kA/m) |
| ISOTROPIC CAST ALNICO | | | | | | | | | | | | | | |
| Alnico 1 | 59 | 12 | 21 | 5 | 3 | — | 1.4 | 11.1 | 7.2 | 720 | 470 | 37 | 480 | 38 |
| Alnico 2 | 55 | 10 | 19 | 13 | 3 | — | 1.7 | 13.5 | 7.5 | 750 | 560 | 45 | 580 | 46 |
| Alnico 3 | 60 | 12 | 25 | — | 3 | — | 1.35 | 10.7 | 7.0 | 700 | 480 | 38 | 500 | 40 |
| ANISOTROPIC CAST ALNICO | | | | | | | | | | | | | | |
| Alnico 5 | 51 | 8 | 14 | 24 | 3 | — | (5.5) | 43.8 | 12.8 | 1280 | 640 | 51 | (640) | 51 |
| Alnico 5DG | 51 | 8 | 14 | 24 | 3 | — | 6.5 | 57.7 | 13.3 | 1330 | 670 | 53 | 670 | 53 |
| Alnico 5-7 | 51 | 8 | 14 | 24 | 3 | — | 7.5 | 59.7 | 13.5 | 1350 | 740 | 59 | 740 | 59 |
| Alnico 6 | 48 | 8 | 16 | 24 | 3 | 1 | 3.9 | 31.0 | 10.5 | 1050 | 780 | 62 | 800 | 64 |
| Alnico 8 | 34 | 7 | 15 | 35 | 4 | 5 | 5.3 | 42.2 | 8.2 | 820 | 1650 | 131 | 1860 | 148 |
| Alnico 8HC | 29 | 8 | 14 | 38 | 3 | 8 | 5.0 | 39.8 | 7.2 | 720 | 1900 | 151 | 2170 | 173 |
| Alnico 9 | 34 | 7 | 15 | 35 | 4 | 5 | 9.0 | 71.6 | 10.6 | 1060 | 1500 | 119 | 1500 | 119 |
| ISOTROPIC SINTERED ALNICO | | | | | | | | | | | | | | |
| Alnico 2 | 52 | 10 | 19 | 13 | 3 | 3 | 1.5 | 11.9 | 7.1 | 710 | 550 | 44 | 570 | 45 |
| ANISOTROPIC SINTERED ALNICO | | | | | | | | | | | | | | |
| Alnico 5 | 48 | 8 | 14 | 24 | 3 | 3 | 3.9 | 31.0 | 10.9 | 1090 | 620 | 49 | 630 | 50 |
| Alnico 6 | 47 | 8 | 15 | 24 | 3 | 3 | 2.9 | 23.1 | 9.4 | 940 | 790 | 63 | 820 | 65 |
| Alnico 8 | 35 | 7 | 15 | 35 | 4 | 4 | 4.0 | 31.8 | 7.4 | 740 | 1500 | 119 | 1690 | 134 |
| Alnico 8HC | 35 | 7 | 14 | 38 | 3 | 3 | 4.5 | 4.5 | 6.7 | 670 | 1800 | 143 | 2020 | 161 | of 9.5 mm. This diameter has a cross-sectional area of 70.9 mm$^2$. Even molded caplets featuring the non-round, "double-D" shape, have cross-sectional areas not in excess of 70.9 mm$^2$. This area has apparently been chosen by the pharmaceutical industry as the upper limit for easy swallowability by the general public for nutritional supplements, over-the-counter medicines, and prescription medicines as this cross-sectional area appears repeatedly.

In an exemplary embodiment, the present bariatric caplet is no larger than Ø 9.5 mm. It's noteworthy that empty gelatin capsules in the "000" size (used in the nutritional supplement field) have a diameter of 9.97 mm. In other exemplary embodiment, a bariatric caplet has a diameter of about Ø 10.0 mm (78.5 mm$^2$) or below.

Note in FIG. 10 that one of the cubes 14 has fallen out of the caplet 12 that it actually left behind apertures 18 in the caplet where the cube had been flush with the caplet's surface. An exemplary cube has a dimension across its diagonal of 9.5 mm. In fact, the chamfers 20 on each edge of the cube may have a radius of 4.75 mm (one-half of 9.5 mm) so as to perfectly conform to the outer contour of the caplet.

Cubes are a compromise of shape and volume: it could have a much larger size where the 9.5-mm truncation would have removed a proportionally larger percentage of the cube. As such, it would have appeared more like a sphere than a cube. However, a tessellated aggregate of cubes featuring such a shape has larger liquid voids between them, and this would allow patients to more easily "eat around" their prescription with high-calorie liquid foods such as milkshakes. In an exemplary embodiment, the size is 8.4 mm across the faces. When truncated on a 9.5-mm-spherical radius with 1-mm radiused transitions, it has a volume of 467 mm$^3$.

Foamed Core and Magnet's Mass Limit: Density

Figure 20:
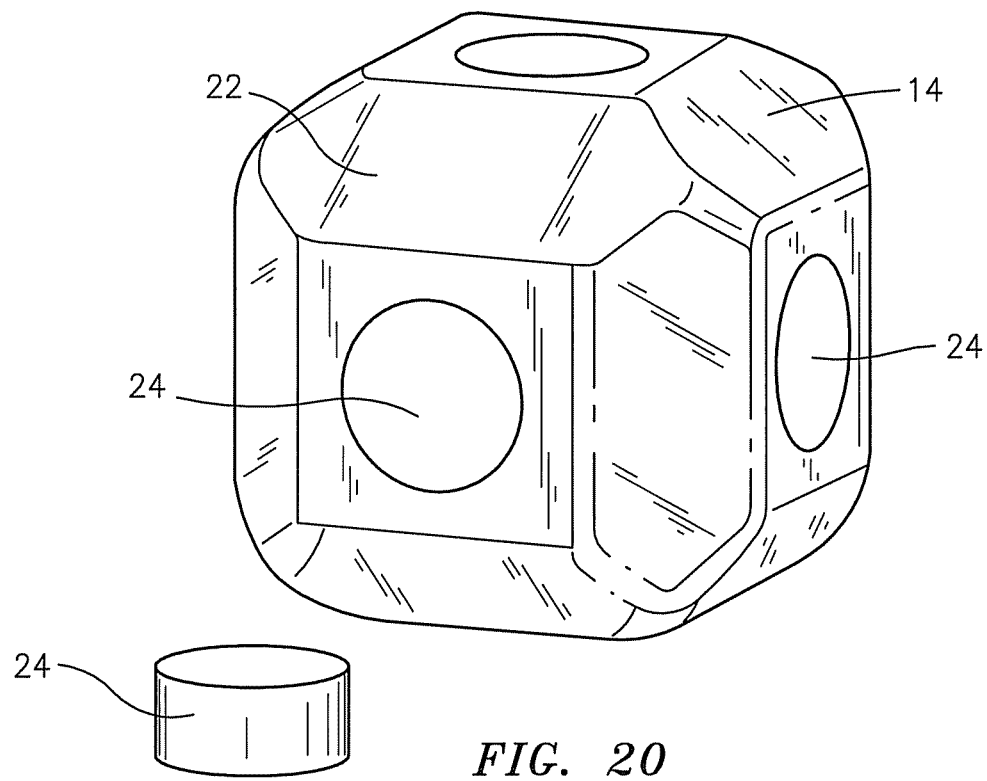
FIG. 20 is a perspective view of an assembled cube utilizing button magnets and an overmolded shell.

FIG. 20 illustrates a foamed core 22 with pressed-in button magnets 24 and a solid, overmolded shell. In an exemplary embodiment, the volume of the entire cube is about 467 mm$^3$. In exemplary embodiments, this volume is an approximate upper limit on how massive the cube with its magnets is: the entire cube with its magnets cannot be so dense that one feels a ponderous weight in their stomach. In exemplary embodiments, an average cube density of $\leq 1.25$ specific gravity is provided. For a volume of 467 mm$^3$, this is a cube mass of $\leq 584$ mg.

One challenge overcome with an exemplary design involves the use of foamed plastic for the core. This achieves decent volume of magnet in a cube when the magnet materials have very high densities in the range of 7.2-8.2. This also overcomes the problem that most plastics have densities in the range of about 0.9-0.95 (even without any magnet material inside the cube whatsoever, plastic cubes would just barely be buoyant to start with). With such dense plastic to mold with, even a small volume of a magnet would greatly weigh down the cubes and cause them to exceed an overall 1.25 specific gravity.

However, the use of foamed plastic for the core in effect, uses a cork-like, buoyant action to help offset the negative buoyancy of the dense magnets. This is why the core in FIG. 20 has the appearance of compressed popcorn. In exemplary embodiments, a foamed core of 50% weight reduction is provided. This permits a magnet mass objective of about 400 mg or below.

The following describes embodiments wherein $\leq 400$ mg magnets are fabricated that are easy to make and overmold, and which have good magnetic attraction.

Shape: the "Jack"

Figure 5:
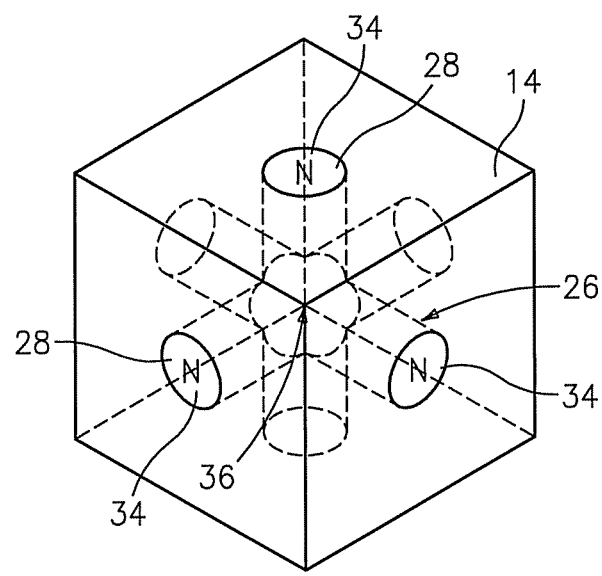
FIG. 5 is a front perspective view illustrating a magnetic apparatus according to a second exemplary embodiment of the present invention.
Figure 6:
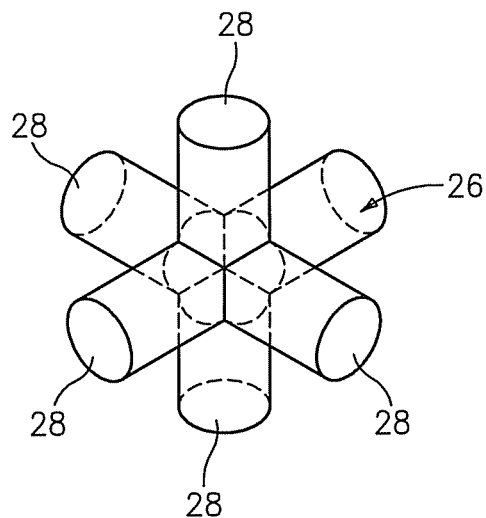
FIG. 6 is a front perspective view illustrating a cavity within a magnetic apparatus according to a second exemplary embodiment of the present invention.
Figure 13:
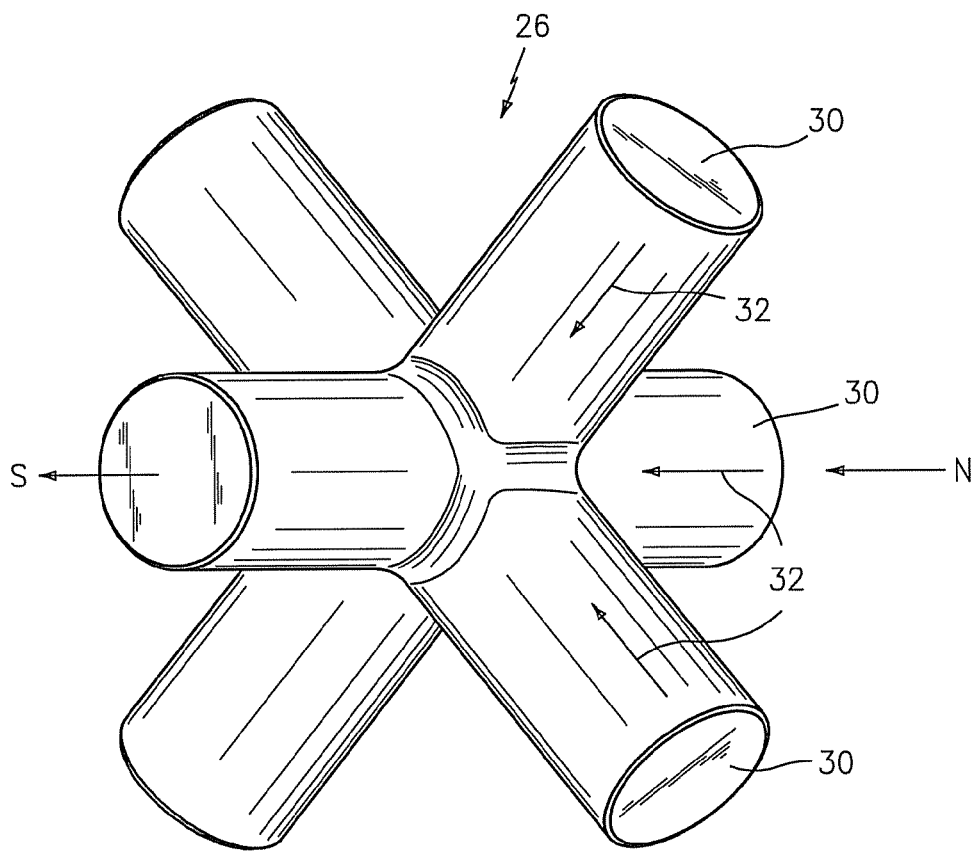
FIG. 13 is a perspective view of an exemplary magnetic jack subjected to a magnetic field.

FIGS. 5 and 6 illustrate a jack 26 configuration. Certain embodiments that entail multiple magnets inside of individual cubes have a drawback from an assembly perspective. That is, it may be difficult to automatically feed them into each of the small cube-shaped cavities inside an injection-molding machine. In an exemplary embodiment, such jack 26 may comprise alnico and samarium-cobalt (although other materials are contemplated herein). The jack of FIG. 6 illustrates a six-pole 28, single-piece "jack"-shaped magnet. FIG. 13 illustrates an exemplary orientation of a magnetizing field for the design. In exemplary embodiments, the jack design of FIG. 6 is configured to result in a design mass of about 400 mg or less.

Magnetizing a Jack: Cast Version

Referring again to FIG. 13, from the point of view of the magnetizing field, it "sees" three legs 30 arranged in a 120° polar star configuration where each leg was tilted back 45° from the field's axis. Though conventional wisdom may reject this design choice (under the assumption that magnets must be two-pole affairs that are always aligned with the field), it has been discovered by the inventor that such design may be readily magnetized. The inventors believe that the material's natural permittivity focus the magnetic field in the same fashion that a solenoid's metal core concentrates the solenoid coil's field (as illustrated in FIG. 13 with the arrows 32 pointing down the legs).

In exemplary embodiments, the magnetized jacks are samarium-cobalt jacks. The inventor has discovered that about $^{17}\!/_{19}$ths saturation may be obtained, e.g., as semi-quantitatively measured by the ability of the jacks to support a chain of 17 paperclips (v.s. the 19 that were held when the components were magnetized while perfectly oriented to the field).

Cast Jack in a Cube

FIG. 5 illustrates a jack 26 fitted into a cube 14. The three north poles 34 (See FIG. 12) results in a cube having a single corner 36 in common with them. In exemplary embodiments, the jack may also be completely isolated from the gastric environment by plastic.

Magnetizing a Jack: Multi-Segment, Pre-Magnetized

In the alternative to cast jacks, jacks may also be fabricated by bonding five separate pieces. Adhesives, tin solder, etc. may be used to bond the pieces.

Figure 12:
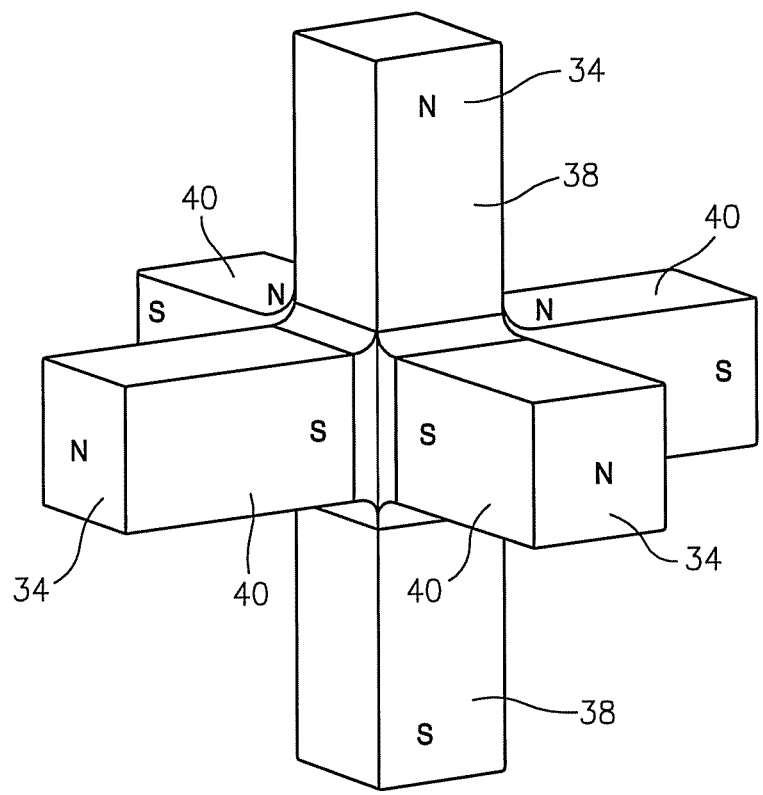
FIG. 12 is a perspective view of an exemplary magnetic jack constructed of individual magnets bonded together.

FIG. 12 shows exemplary magnetic polarities of a five-piece jack made from pre-magnetized components. The vertical portion 38 is a single bar magnet. The four arms 40 are each four individual magnets. The jack assemblies may be fabricated using either of two different methods: 1) out of pre-magnetized bar magnets, or 2) out of non-magnetized components whereby the finished assembly was later exposed to a magnetizing field. The single, vertical pole piece suffered no loss in magnetic strength due to having four other magnets intersecting it at its midsection. What was an unexpected result was that both two-part axis had the magnetic performance of an individual, single-piece bar magnet. This was because the opposing north and south poles at the midsection magnetically coupled very efficiently at the interstitial.

Shape: Diagonal

Figure 8:
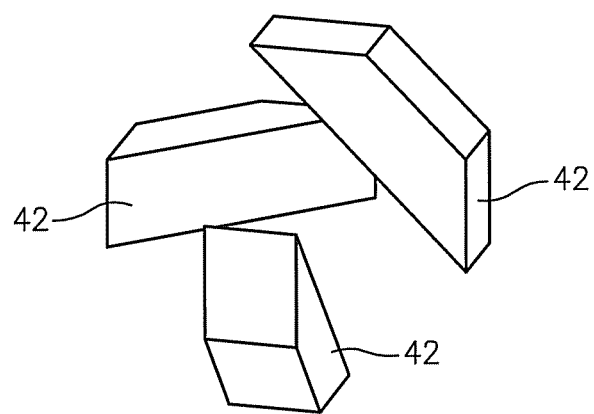
FIG. 8 is a front perspective view illustrating a cavity within a magnetic apparatus according to a third exemplary embodiment of the present invention.
Figure 14:
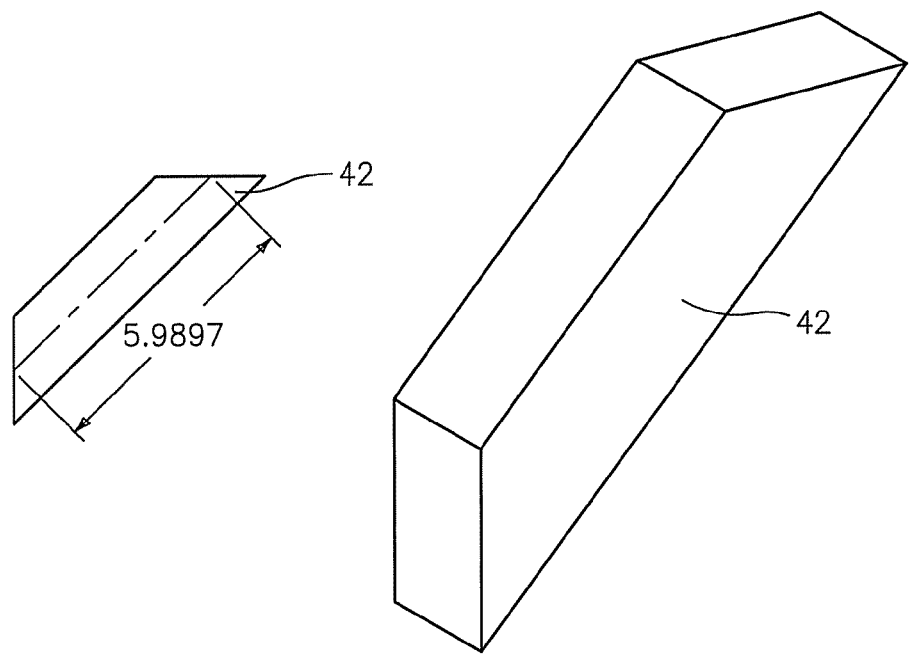
FIG. 14 is a perspective view of an exemplary bariatric magnet having multiple geometric angles.

Before heading into magnetic modeling, other pole orientation concepts were considered. FIGS. 8 and 14 illustrate another exemplary magnet 42 configuration. The illustrated exemplary magnets 42 have a 1.65 mm cross-section, would have had other dimensions as shown in FIG. 14, and would have weighed 404 mg in neodymium (as stated before, all specified dimensions and weights are merely exemplary). As with all other magnet configurations, these poles would have been oriented so three like poles shared a common corner.

Shape: Button Magnets

Figure 7:
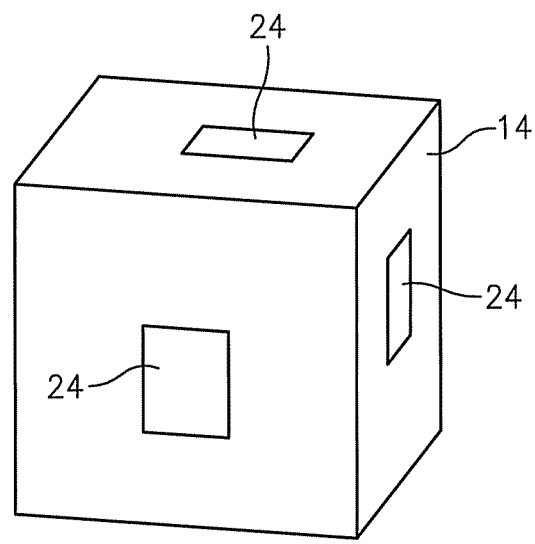
FIG. 7 is a front perspective view illustrating a magnetic apparatus according to a third exemplary embodiment of the present invention.

Another exemplary embodiment comprises a cube 14 with six button magnets 24 (See FIGS. 1-4 and FIG. 20) positioned flush with the surface of the cube 14, where the magnets 24 are attached to the inside surfaces of the mold. Reference is made to FIGS. 1-4, which show various magnetic button configurations. The resulting cube may then be overmolded. For example, six Ø 4.0 mm×0.65 buttons made of 8.3 s.g. material would weigh 407 mg. In order to keep the magnets at least 0.4 mm under the surface after being overmolded, they would have to be 1.0 mm under the final peak surface. It should also be noted that the term "buttons" should not be read to limit the shape of the buttons. Indeed, any convenient shape is contemplated, including, e.g., the rectangular buttons 24 of FIG. 7).

With simple molds, the automation required for handling the magnets is simple: all that is needed is a single, high-speed, continuous-motion (non-incremental) magnet-inserting line capable of handling, e.g., 10 foamed cubes per second. Then the foamed cores with the magnets inserted into them could go back into a different mold to receive the overmolded, clear shell.

Configuring Magnetic Strength

Figure 15:
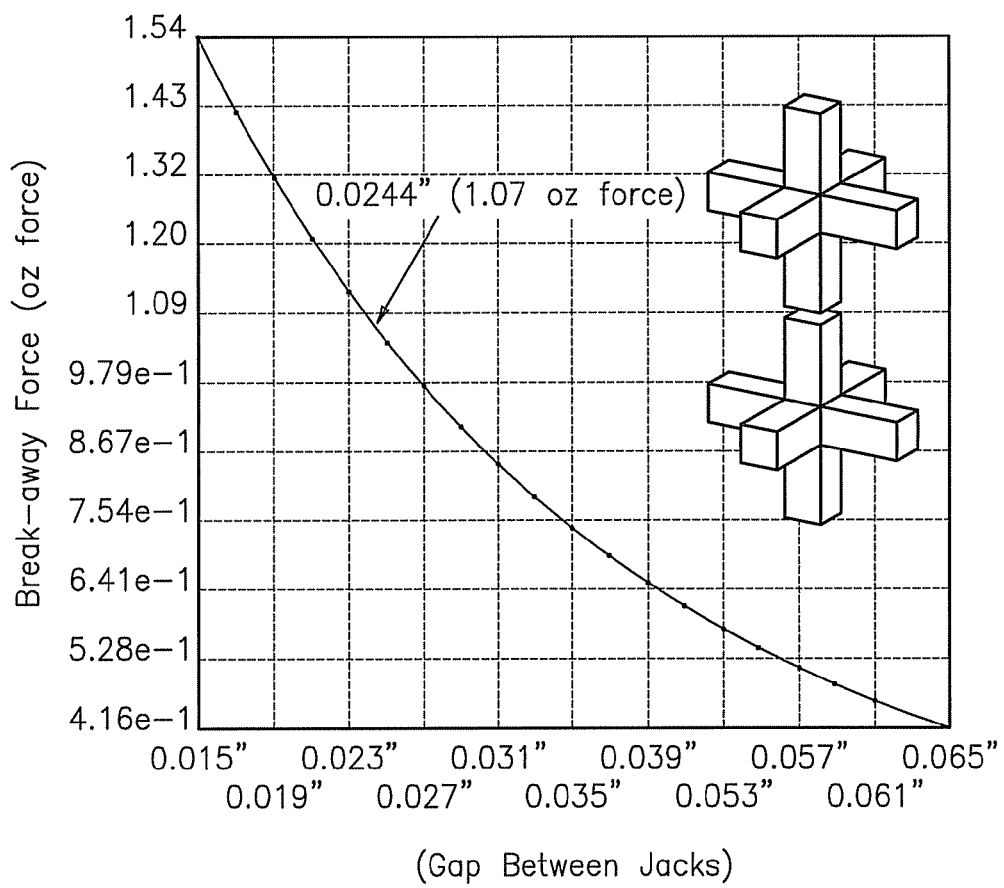
FIG. 15 is graph illustrating the relationship of air gap sizes between adjacent magnetic jacks and the force required to separate the adjacent gaps.

In another exemplary embodiment, the gap (determined by the space between two poles on separate cubes, may be configured to vary the strength of the attraction between separate cubes. Reference is made to FIG. 15, which graphs gap spacing against magnetic attraction, given the assumptions specified by FIG. 15.

With regard to the button magnet concept, the considerations in configuring the attractive force for a given air gap between magnets of any given mass include assessing the aspect ratio: the ratio of a magnet's length divided by its diameter. In general, it may be fairly stated that a long slender magnet exhibits good attractive force from a greater distance (larger air gap), but isn't as efficient with smaller air gaps as would the same mass of magnet with a larger-diameter but a shorter length.

In exemplary embodiments, different length-to-diameter ratios were tested that all equaled 8.917 mm$^3$ to find the aspect ratio that produced maximum inter-magnet attraction with a 0.55 mm gap. The rationale behind a gap of 0.55 mm was an objective of overmolding a clear shell only 0.25 mm thick. This would result in an air gap of 0.50 mm. In a further exemplary embodiment, the gap may be increased the gap to 0.55 mm so the magnets have good pull when pulling "uncooperative" gaps together.

Figure 16:
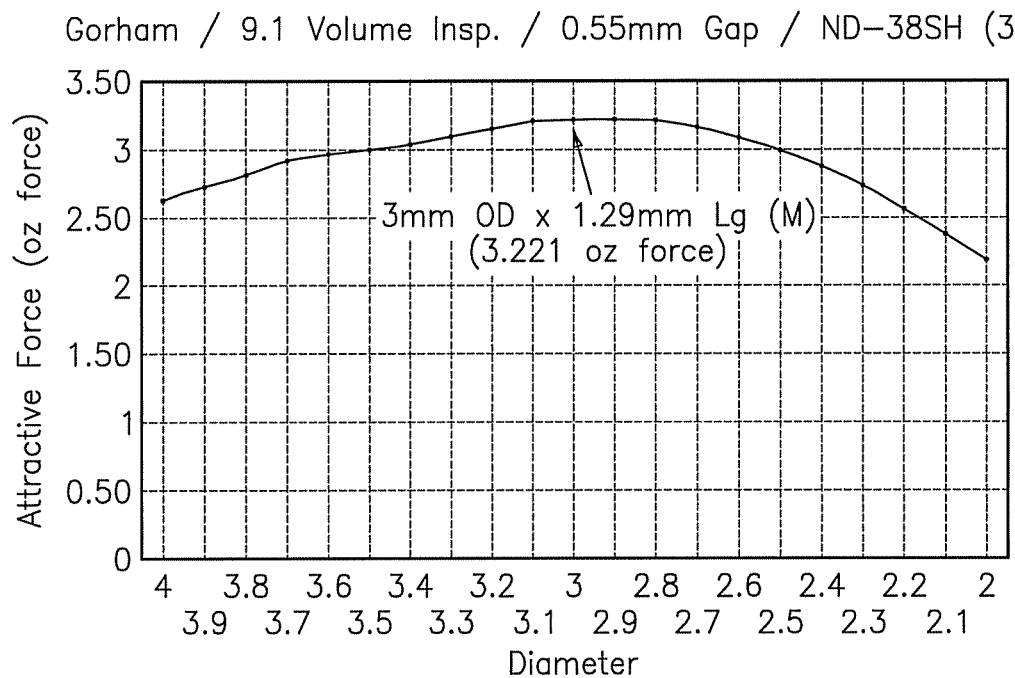
FIG. 16 is a graph correlating the diameter of button magnets with the attractive force between adjacent buttons.

For the modeling, neodymium (N3817-S) was used because it was a medium-strength, commodity-grade neodymium material. FIG. 16 shows that the strongest geometry was Ø 3.0 mm×1.29 mm. This geometry gave a 37° C. (body temperature) pull of 0.920 N (3.31 ounce-force) with two, six-button cubes (FIG. 16 models only two buttons).

More magnetic attraction may be attained by going with more powerful grades (e.g., N4514-M). With a 0.55 mm air gap, the diameter-over-length ratio for a magnet material volume of 8.917 mm$^3$ was Ø 2.90 mm×1.35 mm and a-B/H 1.29 ratio. This yielded a 37° C. pull force of 1.070 N (3.85 ounce-force) @ 0.55 mm, and 1.148 N (4.128 ounce-force) @ 0.50 mm.

A batch of N4514-M button magnets was produced and proved to have an unexpectedly low 7.25 specific gravity. Thus, six Ø 2.90 mm×1.35 mm magnets would weigh 388 mg. This is lighter than the ≦400 mg described previously and allows extra margin for the foamed plastic.

Figure 17:
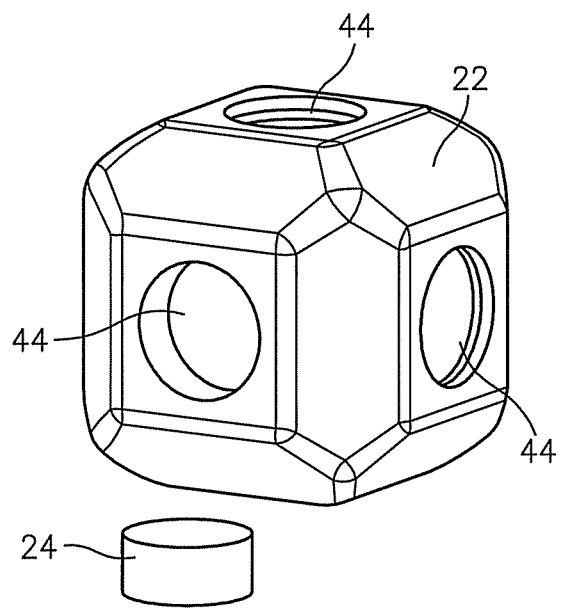
FIG. 17 is a perspective view of a button magnet and cube housing.

Also, with regard to FIGS. 17 and 19, the depth of button pockets 44 in the core 22 may be tailored in an exemplary embodiment so the button magnets 24 would be approximately 0.25 mm below the surface of the cube after the affixing the magnets (e.g., after curing of adhesive).

Isolating the Magnets

Figure 18:
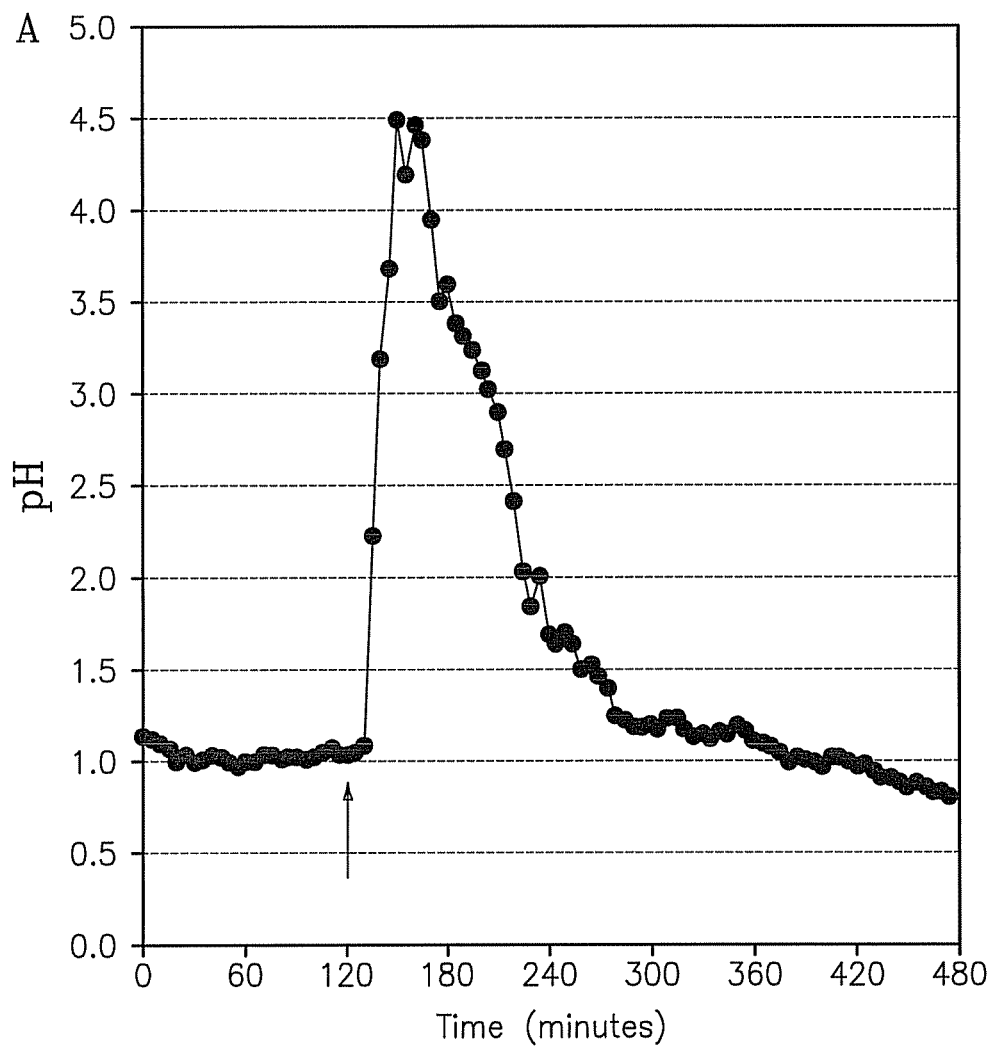
FIG. 18 is a graph correlating the pH of a stomach to the amount of time following ingestion of a meal.

As can be seen in FIG. 18, the human stomach is highly acidic between meals. Cow magnets—magnetic assemblies that reside in ruminants' rumen-reticular chamber to scavenge harmful metallic objects—are made of alnico and do not need a protective coating. This is due to a combination of alnico's corrosion resistance and the higher pH of the numen-reticular chamber.

Magnets, particularly neodymium, cannot completely withstand attack by pH 1 hydrochloric acid (HCl). If large quantities are in the gastric environment at one time, they must be isolated by a physical barrier to prevent overexposure to metals. Still, a certain surface area of certain kinds of magnet materials can be directly exposed to the gastric environment without harm to the patient. For instance, acid exposure tests were performed on alnico 5 and the acid was then analyzed for trace elements. Cobalt was shown to be the limiting constituent. As can be seen in column E in TABLE 2, the limiting exposure for cobalt is 2 mg per day. With alnico, up to 4500 square millimeters of magnet material could be exposed through overmolding defects without risk of harm.

Neodymium and Iron

The situation is different with neodymium: it has advantages and disadvantages. Formulations vary from manufacturer to manufacturer but exemplary grades of neodymium expected for this application are as follows:

Fe=54-64%
Nd=33%
B=1%
Dy=0-10%

Other materials, including without limitation, cobalt, may also be used.

Isolating the Magnets with Parylene

Because neodymium dissolves in HCl faster than other magnet materials, "Parylene C" or the like may be used as a backup coating to the (e.g., 0.25 mm) overmolded shell. Parylene is a vapor-deposited coating that is highly acid resistant and is currently coated over magnets used for implants (such as cochlear implants). Long-term experiments with samarium-cobalt magnets coated with 20 μm (0.8 mil) of Parylene C shows that istexhibits extremely effective, long-term resistance to pH 1.0 HCl at 37° C.

Figure 19:
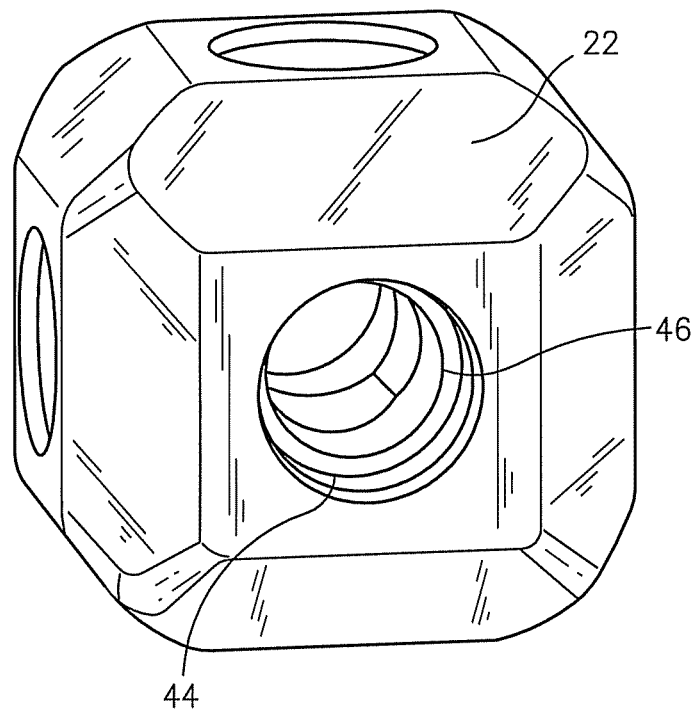
FIG. 19 is a perspective view of a hollow cube housing.

FIG. 19 illustrates another exemplary cube core 22, wherein a Mucell foaming process is used for a fully hollowed-out cube. In such exemplary embodiment, an exemplary core with a mass of about 116 mg may be provided.

Temperature Effects: Overmolding Magnets

Details of what will happen to the magnets while they are being overmolded impact the choice of magnet material. The issue is temperature. For example, for the fully hollowed-out foamed cores 22 of FIG. 19, the holes in the core could have a pocket 44 with an annular step 46 for the magnet to bottom against as it is pressed into the core (see FIG. 19). Behind the magnets, intersecting holes could be used such that additional, unnecessary plastic is eliminated.

Finally, the foamed cores with their inserted button magnets may be overmolded with a thin, clear shell, e.g. of only 0.25 mm thick. When the foamed core and its pressed-in magnets are overmolded, the clear resin may be configured with a high melt temperature, e.g., a melt temperature of around 200° C. (400° F.). The plastic is cooling very rapidly as it flows through the mold's sprues and squeezes into the narrow gap between the foamed core insert and the mold's cavities.

Temperature Effect: Different Grade of Neodymium

Different materials may also be selected based upon temperature resistance, e.g. a temperature resistant grade of neodymium called N4220-SH or N4514-M. Doing so entails making only a small sacrifice in magnetic strength (column A in TABLE 2) but yields a big increase in temperature resistance (column B). We note that when molding the shell, the plastic must be very rapidly injected because it chills extremely quickly when squeezing into the very thin (e/g/. 0.25 mm) gap between the foamed core and the cavity's wall.

In another exemplary embodiment, the multiple-poled magnet is coated with a protective material. In another exemplary embodiment, the multiple-poled magnet is coated with porcelain to protect the magnets from bodily fluids.

In another exemplary embodiment, the magnetic strength of the multiple-poled magnet is between 5.5-45. In another exemplary embodiment, the magnetic strength of the multiple-poled magnet is 5.5.

In another exemplary embodiment, the multiple-poled magnet is demagnetized externally. In another exemplary embodiment, the multiple-poled magnet is demagnetized internally via an endoscopic scope.

While exemplary embodiments have been shown and described, various modifications and substitutions may be made thereto without departing from the spirit and scope of the invention. Accordingly, it is to be understood that the present invention has been described by way of illustration and not limitation.

The invention claimed is:

1. A bariatric procedure, comprising:
   delivering a predetermined, initial dose of a plurality of individual ingestible magnetic, space-filling portions, wherein said portions include a magnetic component having plural magnetic axes, which portions magnetically come together within the stomach of a human patient to form a resulting structure that provides therapeutic bariatric benefit to the patient, further comprising delivering, with said predetermined, initial dose, a predetermined amount of protein/peptide so as to induce closure of the pylorus of the stomach and thereby retain such space-filling portions within the stomach to promote magnetic assembly of the plurality of magnetic, space-filling portions as an initial seed aggregate larger than about 4.8 cm in diameter; and
   subsequently delivering periodic lower predetermined doses of a plurality of individual ingestible magnetic space-filling portions that are provided with a predetermined amount of protein/peptide so as to induce closure of the pylorus of the stomach and thereby retain such space-filling portions within the stomach to promote magnetic assembly of the plurality of magnetic, space-filling portions; wherein the space-filling portion has plural faces and each face is associated with a different magnet.

2. A bariatric procedure in accordance with claim 1, wherein said protein/peptide is provided integrally with at least one of said predetermined, initial dose of a magnetic, space-filling portions.

3. A bariatric procedure in accordance with claim 2, wherein said protein/peptide is configured as a caplet or capsule that at least partially surrounds at least one of said magnetic, space-filling portions.

4. A bariatric procedure in accordance with claim 3, wherein said caplet or capsule encapsulates at least one magnetic, space-filling portion.

5. A bariatric procedure in accordance with claim 4, wherein said caplet or capsule encapsulates two magnetic, space-filling portions.

6. A bariatric procedure in accordance with claim 1, wherein said space-filling portions have a volume of about 0.5 to about 2.2 mL.

7. A bariatric procedure in accordance with claim 1, wherein the resulting structure formed from the space-filling portions has a specific gravity of about 1.0.

8. A bariatric procedure in accordance with claim 1, wherein the resulting structure can be influenced by an exteriorly applied magnetic field, and wherein the application of the exteriorly applied magnetic field in a predetermined pattern causes the structure to move within the patient's body.

9. A bariatric procedure in accordance with claim 1, wherein the space-filling portions have an exterior surface which is formed from a material which is substantially biologically inert.

10. A bariatric procedure in accordance with claim 1, wherein said protein/peptide is provided separately, but concurrently with said plurality of magnetic space-filling portions.

11. A bariatric procedure in accordance with claim 10, wherein said protein/peptide is provided in caplet or capsule form.

12. A bariatric apparatus, comprising:
    an ingestable magnetic, space-filling portion, wherein said portion includes a magnetic component having plural magnetic axes, which portion is configured to magnetically come together within the stomach of a human patient with other such ingestible, magnetic, space-filling portions to form a resulting structure that provides therapeutic bariatric benefit to the patient, wherein the space-filling portion is provided with a predetermined amount of protein/peptide so as to induce closure of the pylorus of the stomach and thereby retain such space-filling portions within the stomach to promote magnetic assembly of the plurality of magnetic, space-filling portions; wherein the space-filling portion has plural faces and each face is associated with a different magnet.

13. A bariatric apparatus in accordance with claim 12, wherein said protein/peptide is provided integrally with at least one magnetic, space-filling portion.

14. A bariatric apparatus in accordance with claim 13, wherein said protein/peptide is configured as a caplet or capsule that at least partially surrounds at least one magnetic, space-filling portion.

15. A bariatric apparatus in accordance with claim 14, wherein said caplet or capsule encapsulates at least one magnetic, space-filling portion.

16. A bariatric apparatus in accordance with claim 15, wherein said caplet or capsule encapsulates two magnetic, space-filling portions.

17. A bariatric apparatus, comprising:
    an ingestable magnetic, space-filling portion having plural faces, which portion is configured to magnetically come together within the stomach of a human patient with other such ingestible, magnetic, space-filling portions to form a resulting structure, wherein the portion containing a magnetic component such that each face is associated with a different magnet.

18. A bariatric apparatus in accordance with claim 17, wherein said magnetic component comprises a jack-shaped component comprising a cast jack that is magnetized to create a magnet on each arm of the jack.

19. A bariatric apparatus in accordance with claim 17, wherein said magnetic component comprises a bonded jack shaped component with a magnet on each arm of the jack.

20. A bariatric apparatus in accordance with claim 18, wherein the jack shaped component is singly cast and then magnetized.

21. A bariatric apparatus in accordance with claim 17, wherein said portion includes six faces with six magnetic buttons provided in a core member to form the space-filling portion.

22. A bariatric apparatus in accordance with claim 21, wherein the core member comprises a foamed polymer material.

23. A bariatric apparatus in accordance with claim 22, wherein the foamed polymer material includes a hollow interior and a button seat configured to retain the magnetic button in a predetermined position.

24. A bariatric apparatus in accordance with claim 22, further comprising an overmolded shell provided over the seated magnetic buttons and core.

25. A bariatric apparatus in accordance with claim 17, wherein said said portion includes eight faces with a magnet associated with each of said eight faces.

\* \* \* \* \*